United States Patent [19]

Kaiser

[11] 4,351,767

[45] Sep. 28, 1982

[54] SYNTHESIS OF 24,25-DIHYDROXYCHOLESTEROL

[76] Inventor: Emil T. Kaiser, 5634 S. Woodlawn Ave., Chicago, Ill. 60637

[21] Appl. No.: 278,838

[22] Filed: Jun. 29, 1981

[51] Int. Cl.³ .............................................. C07J 71/00
[52] U.S. Cl. ........................ 260/239.55 R; 260/397.2
[58] Field of Search ........................ 260/239.55, 397.2

[56] References Cited

U.S. PATENT DOCUMENTS 4,145,357  3/1979  Ochi et al. ........................ 260/397.2
4,183,852  1/1980  Kaiser ............................... 260/397.2

Primary Examiner—Elbert L. Roberts
Attorney, Agent, or Firm—Carl C. Batz

[57] ABSTRACT

This invention relates to the synthesis of steroids which are useful for their biological activity or which may be converted to steroids which have such activity. More particularly, the invention pertains to the synthesis of 24,25-dihydroxycholesterol. It includes intermediate sterols of this synthesis and processes for their preparation.

12 Claims, No Drawings

SYNTHESIS OF 24,25-DIHYDROXYCHOLESTEROL

BACKGROUND

Hyodeoxycholic acid is a principal component of animal bile. In my U.S. Pat. No. 4,217,279, I disclose the transformation of hyodeoxycholic acid into 24-carbon steroid alcohols with protected hydroxyl functions in the 3α- and 6α-positions; and in my U.S. Patent Application Ser. No. 236,160, filed Feb. 20, 1981, I disclose transformation to the corresponding aldehydes.

SUMMARY

I have now discovered syntheses by which the sterol aldehyde derived from hyodeoxycholic acid, and disclosed in my U.S. Patent Application Ser. No. 236,160, may be transformed to 24, 25-dihydroxycholesterol. The intermediate sterols and the steps of this transformation will be described as follows:

DESCRIPTION OF THE INVENTION

The synthesis starts with a 24-carbon steroid-24-aldehyde with protected hydroxyl groups in the 3α- and 6α-position, having the structure:

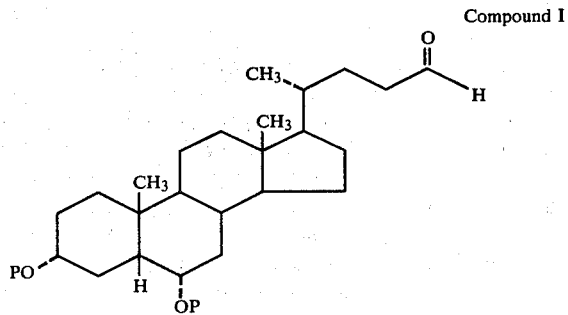

Compound I where P is 2-tetrahydropyranyl (2-THP), β-methoxyethoxymethyl (β-MEM), tertiary butyl (t-Bu), trimethylsilyl ($Me_3Si$) or t-butyldimethylsilyl )t-$BuMe_2Si$). Where P is 2-tetrahydropyranyl, this may be written: 3α, 6α-bis(2-tetrahydropyranyloxy)-5β-cholane-24-al.

In Step 1, in which a Wittig reagent is used, Compound I may be reacted in the same manner, regardless of the nature of the P protecting groups.

Step 1. The Wittig reagent may be prepared by mixing a suspension of trimethylphosphonium bromide in tetrahydrofuran with a solution of n-butyllithium in hexane. This ylid solution may be mixed with a solution in tetrahydrofuran of Compound I, and the mixture stirred and then refluxed until the reaction is complete to obtain the compound having the structure:

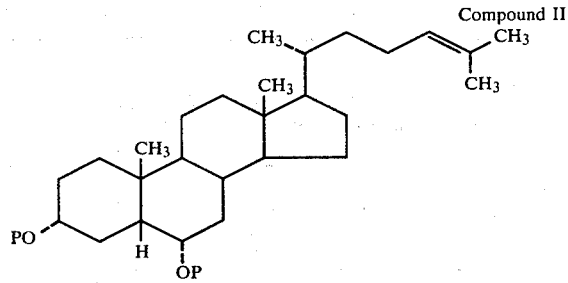

Compound II where P is 2-THP, β-MEM, t-Bu, $Me_3Si$ or t-$BuMe_2Si$. Where P is 2-THP, this may be written: 3α, 6α-bis(2-tetrahydropyranyloxy)-5β-cholest-24-ene.

Step 2. The P-protecting groups may be removed. When P is 2-THP, t-Bu, $Me_3Si$ or t-$BuMe_2Si$, Compound II may be dissolved in ethanol, p-toluenesulfonic acid and water added, and the solution refluxed until the 3α- and 6α-hydroxyl groups are restored. When P=β-MEM, the protecting groups may be removed by dissolving Compound II in methylene chloride containing a one to six-carbon alcohol in a concentration up to 5% and stirring said solution with zinc bromide until the 3α- and 6α-hydroxyl groups are restored.

The resulting compound may have the structure:

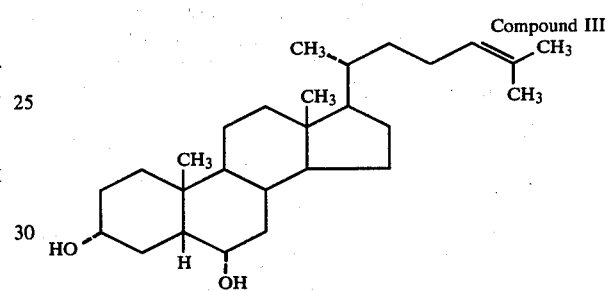

Compound III which may be written:
3α, 6α-dihydroxy-5β-cholest-5-ene.

Step 3. Compound III may be dissolved in pyridine, and the solution mixed with p-toluenesulfonyl chloride and stored in a refrigerator at a temperature of the order of 4° C. until the formation of the p-toluenesulfonyl ester (p-TsO) is complete to obtain the compound having the structure:

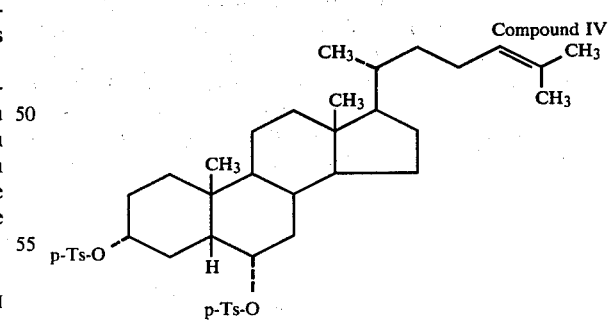

Compound IV which may be written:
3α, 6α-ditosyloxy-5β-cholest-24-ene.

Step 4. Compound IV may be dissolved in methylene chloride and mixed with a solution of m-chloroperbenzoic acid. The resulting solution may be stored until the reaction is complete to obtain the compound having the structure:

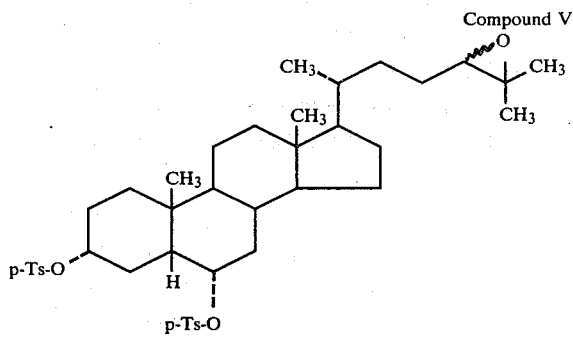

Compound V which may be written:

3α, 6α-ditosyloxy-5β-cholest-24-ene oxide. The epoxy ring in the 24R- and 24S-configurations being indicated by the designation.

Step 5. Compound V may be dissolved in tetrahydrofuran, the solution mixed at a temperature of the order of 0° C. with a 3 N-aqueous sulfuric acid solution and stirred at about 0° C. for a period of up to 1 hour and then at room temperature for up to 30 minutes to obtain the compound having the structure:

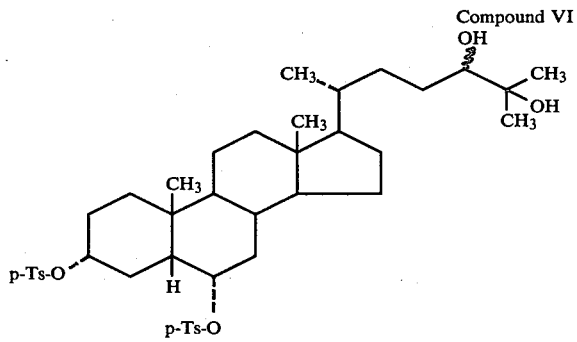

Compound VI with the 24-hydroxy in the 24R- and 24S-configuration, which may be written:

24ε, 25-dihydroxy-3α, 6α,-ditosyloxy-5β-cholestane.

Step 6. Compound VI and potassium acetate may be mixed with dimethylformamide containing about 10% water. The resulting solution may be heated to 100°-110° C. for about 4 hours and mixed with two to three volumes of cold dilute hydrochloric acid. The resulting precipitate may be removed by filtration, suspended in water and refluxed with a methanolic potassium hydroxide solution to obtain a mixture of 24R, 25- and 24S, 25-dihydroxycholesterol which has the structure:

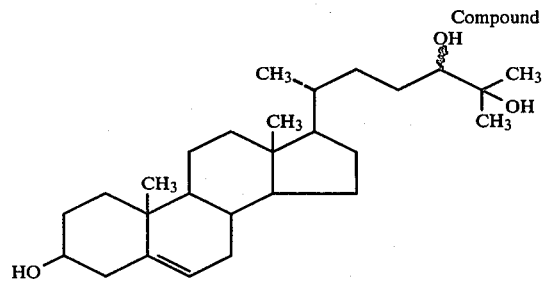

Compound VII

Alternately, the transformation from Compound V to Compound VII may be accomplished by introducing a double bond between positions 5 and 6 and subjecting the resulting compound to Steps 5 and 6 as above described, including treatment with potassium acetate, acid treatment and saponification. This alternative process is the same as the process first described except for a change in the sequence of the treatments.

Following are specific examples in which my invention was carried out in the preparation of sterols which either have biological activity or which may be converted to sterols having such activity:

EXAMPLE I

Preparation of 3α,6α-bis(2-tetrahydropyranyloxy)-5β-cholest-24-ene

Methyl hyodeoxycholate was reacted with 2,3-dihydropyran in dioxane solution in the present of p-toluenesulfonic acid as catalyst in accordance with the procedure described in my U.S. Pat. No. 4,217,279. The methyl 3α,6α-bis(2-tetrahydropyranyloxy)hyodeoxycholate so obtained was reduced with an alkaline reducing agent to the 24-hydroxy-3α,6α-bis(2-tetrahydropyranyloxy)-5β-cholane. The 24-hydroxyl group was oxidized to a 24-aldehyde group, according to the procedure described in my U.S. patent application Ser. No. 236,160, to produce 3α,6α-bis(2-tetrahydropyranyloxy)-5β-cholane-24-al.

An ylid solution was prepared by adding dropwise 2.1 ml of a solution of 1.5 M n-butyllithium in hexane to a suspension of 1 g of isopropyl triphenylphosphonium bromide in 20 ml of dry tetrahydrofuran. The mixture was stirred for an additional 30 minutes at room temperature. A solution of 1.42 g of 3α,6α-bis(2-tetrahydropyranyloxy)-5β-cholane-24-al in 5 ml of tetrahydrofuran was added dropwise, with stirring, to the deep red ylid solution. The color turned from red to light orange. Stirring at room temperature was continued for 2 hours, and then the solution was refluxed for 2 hours. After cooling, the solvents were removed under reduced pressure, and the residue dissolved in a 20 ml 90% methanol-10% water mixture. This aqueous methanol solution was twice extracted with 20 ml portions of petroleum ether, the combined petroleum ether extracts washed successively with aqueous methanol and with a saturated sodium chloride solution. The petroleum ether solution was dried, the solvent evaporated, and the residue dried under reduced pressure. At this point, 1.20 g of a residue remained, which from nmr data was identified as 3α,6α-bis(2-tetrahydropyranyloxy)-5β-cholest-24-ene.

Larger scale runs were also carried out, and the results are listed in the following table:

| Isopropyl-triphenyl-phosphonium bromide (g) | n-BuLi solution (ml) | Compound I, P = THP (g) | Compound II, P = THP product (g) | Yield (%) |
|---|---|---|---|---|
| 3.08 | 5.3 | 4.35 | 3.6 | 79 |
| 18.74 | 33.0 | 26.50 | 21.3 | 77 |
| 26.24 | 47.0 | 37.00 | 32.9 | 85 |
| 22.50 | 37.0 | 28.40 | 27.0 | 91 |

EXAMPLE II

Preparation of 3α,6α-bis(β-methoxyethoxymethoxy)-5β-cholesten-24-ene 1.4 g of 3α,6α-bis(β-methoxyethoxymethoxy)-5β-cholan-24-al (prepared as described in my U.S. patent application Ser. No. 236,160) was dissolved in 5 ml of tetrahydrofuran, and this solution was added dropwise to the deep red ylid solution (as described in Example I), and the chain extension reaction carried out in the same manner as in Example I. The residue remaining after evaporation of petroleum ether was the 3α,6α-bis(β-methoxyethoxymethoxy)-5β-cholest-24-ene.

EXAMPLE III

Preparation of 3α,6α-bis(t-butyloxy)-5β-cholest-24-ene

A solution of 3α,6α-bis(t-butyloxy)-5β-cholen-24-al (prepared as described in my U.S. patent application Ser. No. 236,160) was dissolved in 5 ml of tetrahydrofuran and added dropwise to the ylid solution (described in Example I). The mixture was stirred for 2 hours and then the solution was refluxed for 2 hours. After evaporation of the solvent, the residue was dissolved in a 90% methanol-10% water mixture, extracted with petroleum ether and the petroleum ether extract evaporated. The residue was identified by NMR and IR data as the 3α,6α-bis(t-butyloxy)-5β-cholest-24-ene.

EXAMPLE IV

Preparation of 3α,6α-bis(trimethylsilyloxy)-5β-cholest-24-ene 1.4 g of 3α,6α-bis(trimethylsilyloxy)-5β-cholen-24-al (prepared as described in my U.S. patent application Ser. No. 236,160) was dissolved in 5 ml of tetrahydrofuran and added dropwise to the ylid solution, as described in Example I. The reaction mixture was processed in the same manner as described in Example I, and the production remaining after the evaporation of the petroleum ether solvent was identified by IR and NMR data as 3α,6α-bis(trimethylsilyloxy)-5β-cholest-24-ene.

EXAMPLE V

Preparation of 3α,6α-bis(dimethyl-t-butylsilyloxy)-5β-cholest-24-ene 1.4 g of 3α,6α-bis(dimethyl-t-butylsilyloxy)-5β-cholen-24-al (prepared as described in my U.S. patent application Ser. No. 236,160) was dissolved in 5 ml of tetrahydrofuran and added dropwise to the ylid solution (as described in Example I). The reaction mixture was stirred, refluxed and processed in the manner of Example I. The product remaining after the evaporation of the petroleum ether extract was identified by IR and NMR data as the 3α,6α-bis (dimethyl-t-butylsilyloxy)-5β-cholest-24-ene.

EXAMPLE VI

Hydrolysis of 3α,6α-bis(2-tetrahydropyranyloxy)-5β-cholest-24-ene 27.0 g of 3α,6α-bis(2-tetrahydropyranyloxy)-5β-cholest-5-ene was added to a mixture of 540 ml of ethanol and 160 ml of water containing 2.61 g of p-toluenesulfonic acid. After 2½ hours of refluxing, the solution was cooled, neutralized with approximately 1 ml of 29% ammonia and mixed with 270 ml of hexane and 270 ml of water. After separation of the hexane layer, the ethanol-water layer was extracted again with two 270 ml portions of hexane. The hexane extracts were combined, washed with 500 ml of sodium chloride solution, dried and evaporated to dryness. The remaining solid was mixed with 200 ml of petroleum ether, the solid collected by filtration and dried; and 9.75 g of 3α,6α-dihydroxy-5β-cholest-24-ene, identified by IR and NMR data, was obtained; yield was 51%.

EXAMPLE VII

Hydrolysis of 3α,6α-bis(t-butyloxy)-5β-cholest-24-ene 27 g of 3α,6α-bis(t-butyloxy)-5β-cholest-24-ene was mixed with 540 ml of ethanol and 160 ml of water containing 2.61 g of p-toluenesulfonic acid. As in Example VI, the solution was refluxed, neutralized with ammonia, diluted with water and extracted with hexane. The hexane extract was washed, dried and evaporated to dryness. The residue is the 3α,6α-dihydroxy-5β-cholest-5-ene, shown by IR and NMR data as being identical with the compound obtained in Example VI.

EXAMPLE VIII

Hydrolysis of 3α,6α-bis(trimethylsilyloxy)-5β-cholest-24-ene 27 g of 3α,6α-bis(trimethylsilyloxy)-5β-cholest-24-ene was mixed with 250 ml of ethanol and 160 ml of water containing 2.61 g of p-toluenesulfonic acid. As in Example VI, the solution was refluxed, neutralized with ammonia, diluted with water and extracted with hexane. The hexane extract was washed, dried, and evaporated to dryness. The residue was 3α,6α-dihydroxy-5β-cholest-24-ene; and, as shown by IR and NMR data, was identical with the compound obtained in Example VI.

EXAMPLE IX

Hydrolysis of 3α,6α-bis(dimethyl-t-butylsilyloxy)-5β-cholest-24-ene 27 g of 3α,6α-bis(dimethyl-t-butylsilyloxy)-5β-cholest-24-ene was mixed with 540 ml of ethanol and 160 ml of water containing 2.61 g of p-toluenesulfonic acid. As in Example VI, the solution was refluxed, neutralized with ammonia, diluted with water and extracted with hexane. The hexane extract was washed, dried, and evaporated to dryness. The residue was the 3α,6α-dihydroxy-5β-cholest-24-ene, and was shown by IR and NMR data to be identical with the compound obtained in Example VI.

EXAMPLE X

Preparation of 3α,6α-dihydroxy-5β-cholest-24-ene 2.0 g of 3α,6α-bis(β-methoxyethoxymethoxy)-5β-cholest-24-ene, prepared according to Example V, was dissolved in a mixture of 20 ml of methylene chloride and 0.30 ml of methanol, and the solution was stirred with 5 g of zinc bromide for 18 hours. Then, ether was added, the mixture washed with water, the organic layer dried, the solvent evaporated, the residue washed with petroleum ether and dried. From nmr and ir data, the residue was identified as 3α,6α-dihydroxy-5β-cholest-24-ene, the same product as obtained by the acid hydrolysis of the 2-THP, t-Bu, Me$_3$Si and Me$_2$t-BuSi ethers in Examples VI–IX.

EXAMPLE XI

Preparation of 3α,6α-ditosyloxy-5β-cholest-24-ene 3.5 g of 3α,6α-dihydroxy-5β-cholest-24-ene and 10.2 g of p-toluenesulfonyl chloride were dissolved in 90 ml of dry pyridine and then kept in a refrigerator for 48 hours. The mixture was poured into 300 ml of ice-water and the pH adjusted to 3 by adding concentrated HCl. After stirring for 30 minutes, the precipitate was removed by filtration, washed 4 times with 100 ml portions of water and dissolved in 300 ml of chloroform. The chloroform solution was washed with 30 ml of 5% sodium bicarbonate solution, four times with 50 ml of water solution, and dried. The solvent was evaporated and the residue dried. The yield was 5.1 g of a white solid (83%) identified from ir and nmr data as 3α,6α-ditosyloxy-5β-cholest-24-ene.

EXAMPLE XII

Preparation of 3α,6α-ditosyloxy-5β-cholest-24-ene oxide

To a solution of 1 g of 3α,6α-ditosyloxy-5β-cholest-24-ene in 15 ml of methylene chloride, 0.35 g of m-chloroperbenzoic acid, dissolved in 7.5 ml of methylene chloride, was added to 0° C. under a blanket of nitrogen. The reaction mixture was stirred for 1 hour at 0° C., then for 16 hours at room temperature. After dilution with 190 ml of methylene chloride, the solution was washed with 50 ml of a 4% sodium bisulfite solution, 50 ml of water, 50 ml of 5% sodium bicarbonate solution and, finally, with 50 ml of a saturated sodium chloride solution. The organic layer was dried, the solvent removed under reduced pressure, and the residue dried. The 3α-6α-ditosyloxy-5β-cholest-24-ene oxide was obtained as a pale yellow solid, weighing 0.61 g.

The process was repeated with larger amounts, and the following results were obtained:

| Compound IV- (g) | m-chloroperbenzoic acid, 85% (g) | $CH_2Cl_2$ (ml) | Compound V (g) | Yield % |
|---|---|---|---|---|
| 0.95 | 0.35 | 15 & 7.5 | 0.65 | 67 |
| 4.7 | 1.65 | 71 & 35 | 4.00 | 83 |
| 9.6 | 3.38 | 150 & 70 | 9.4 | 96 |

EXAMPLE XIII

Preparation of 24ε, 25-dihydroxy-3α,6α-ditosyloxy-5β-cholestane

To a solution of 7.95 g of 3α,6α-ditosyloxy-5β-cholest-24-ene oxide in 150 ml of tetrahydrofuran, 50 ml of 3 N-sulfuric acid was added at 0° C. The mixture was stirred for 1 hour at 0° C., then for 30 minutes at room temperature. A mixture of ice and water was added, followed by methylene chloride. The organic layer was separated, washed with water, aqueous sodium bicarbonate solution and with a saturated sodium chloride solution. After drying, the solvent was evaporated and the residue dried. The yield of 24ε, 25-dihydroxy-3α,-6α-ditosyloxy-5β-cholestane was 6.75 g, 83%. The 24ε designation signifies that this compound is a mixture of the 24R and 24S-epimers as shown from ir and nmr data.

EXAMPLE XIV

Preparation of 24ε,25-dihydroxycholesterol

To a mixture of 30 ml of dimethylformamide and 3 ml of water, 1.84 g of 24ε, 25-dihydroxy-3α,6α-ditosyloxy-5β-cholestane and 2.43 g of potassium acetate were added. The mixture was stirred and heated to 109° C., kept at that temperature for 4 hours, cooled, and then poured into 70 ml of cold 5% hydrochloric acid. The resulting precipitate was collected on a filter, washed with water, and then suspended in 30 ml of 4% methanolic potassium hydroxide solution. After 2 hours of refluxing, the solution was cooled and the alkali neutralized with dilute hydrochloric acid. The mixture was evaporated to dryness, the residue extracted with methylene chloride, and the solvent evaporated. The residue, as shown from nmr and ir data, was a mixture of 24R, 25- and 24S, 25-dihydroxycholesterol. The yield was 0.77 mg (75%). NMR (CD Cl₃), positions of protons indicated in parenthesis: 85.32 (brd, C-6), 3.5 (m, C-3), 3.31(brt,C-24), 1.21(s,C-27), 1.16(s,C-26), 1.01 (s,C-19), 0.93(d,C-21), 0.69(s,C-18).

EXAMPLE XV (Alternate pathway, Compound V-VII)

Preparation of 24ε,25-dihydroxycholesterol from 3α,6α-ditosyloxy-5β-cholest-24-ene oxide To a mixture of 30 ml of dimethylformamide and 33 ml of water, 1.84 g of 3α,6α-ditosyloxy-5β-cholest-24-ene oxide and 2.43 g of potassium acetate were added. The mixture was stirred and heated to 109° C., kept at that temperature, cooled, and then poured into 70 ml of ice cold 5% sulfuric acid. The resulting mixture was extracted with methylene chloride, the organic layer washed with water, aqueous sodium bicarbonate and with saturated NaCl solution, dried, and the solvent evaporated under reduced pressure. The residue was dissolved in 35 ml of tetrahydrofuran, and 12 ml of 3 N sulfuric acid was added at 0° C. The mixture was stirred for 30 minutes at room temperature and diluted with ice cold water. The mixture was evaporated. The residue was a mixture of 24R, 25- and 24S,25-dihydroxycholesterol epimers, the same mixture as was obtained in Example XIV.

While only certain embodiments of my invention are disclosed in detail, it will be apparent to those skilled in the art that many embodiments may be practiced and many changes may be made, all within the spirit of the invention and the scope of the appended claims.

What I claim is:

1. A compound having the structure:

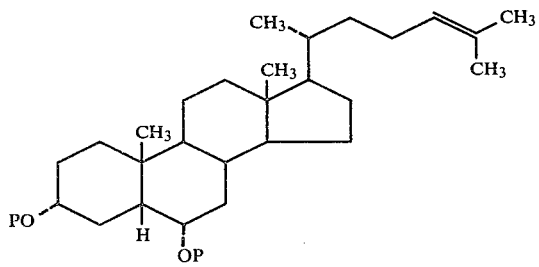

where P is 2-tetrahydropyranyl, β-methoxyethoxymethyl, tertiary-butyl, trimethylsilyl or tertiary-butyldimethylsilyl.

2. The compound of claim 1 where P is 2-tetrahydropyranyl.

3. The compound of claim 1 where P is β-methoxyethoxymethyl.

4. A compound having the structure:

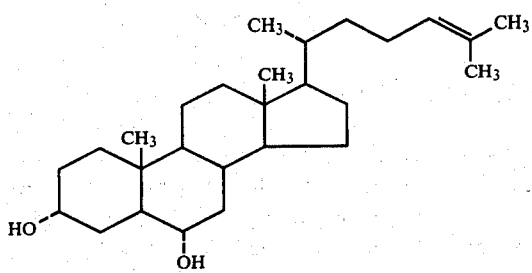

5. A compound having the structure:

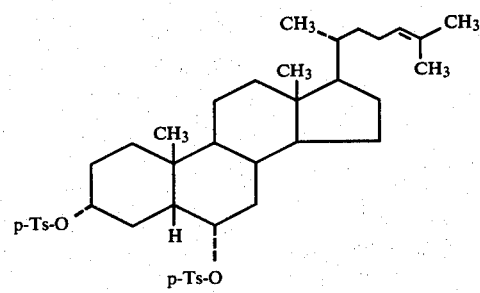

where p-Ts=p-toluenesulfonyl.

6. A compound having the structure:

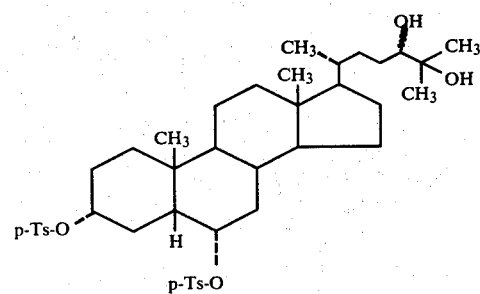

where p-Ts=p-toluenesulfonyl.

7. A compound having the structure:

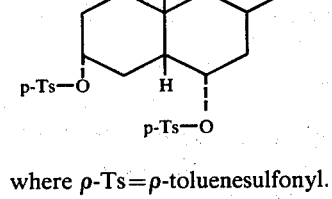

where ε stands for R- and S-configurations.

8. In a process for preparing a steroid derivative, the step of mixing:

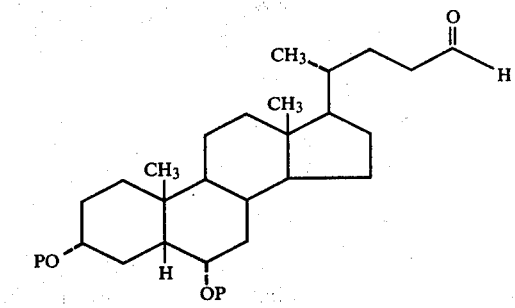

where P is 2-tetrahydropyranyl, β-methoxyethoxymethyl, tertiary-butyl, trimethylsilyl or tertiary-butyldimethylsilyl with an ylid reagent prepared from trimethylphosphonium bromide in tetrahydrofuran and n-butyllithium in hexane, said compound being dissolved in tetrahydrofuran, stirring and refluxing said mixture until the reaction is completed to prepare the compound:

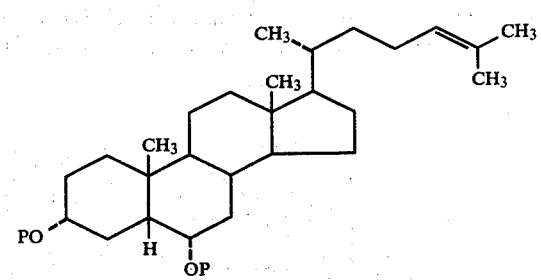

where P is 2-tetrahydropyranyl, β-methoxyethoxymethyl, tertiary-butyl, trimethylsilyl or tertiary-butyldimethylsilyl.

9. In a process for preparing a steroid derivative, the step of refluxing:

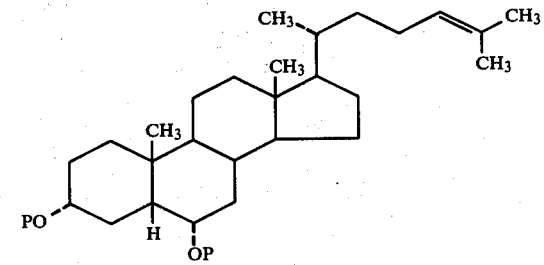

where P is 2-tetrahydropyranyl, tertiary-butyl, trimethylsilyl or tertiary-butyldimethylsilyl, in an ethanol-water mixture, with p-toluenesulfonic acid to prepare the compound:

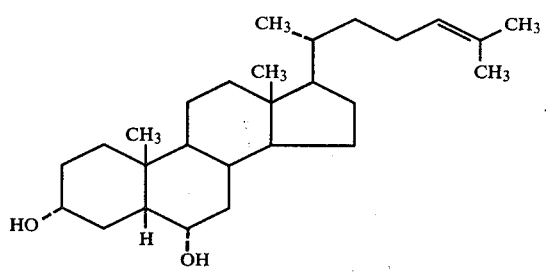

10. In a process of preparing a steroid derivative, the step of stirring:

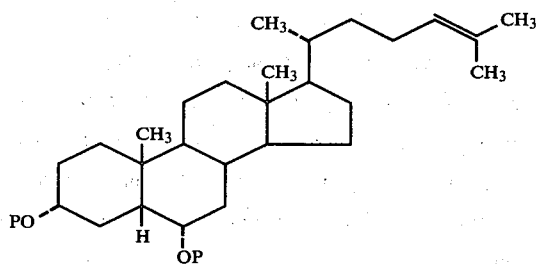

where P is β-methoxyethoxymethyl, in methylene chloride solution containing a 1–6 carbon alcohol in a concentration up to 6%, with zinc bromide to prepare the compound:

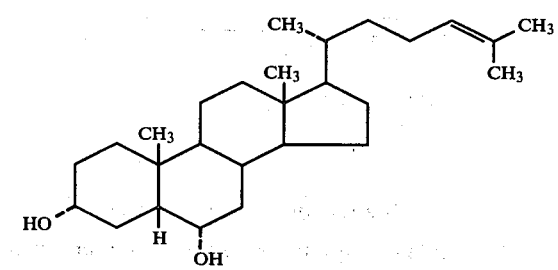

11. In a process for preparing a sterol derivative, the step of mixing a compound having the structure:

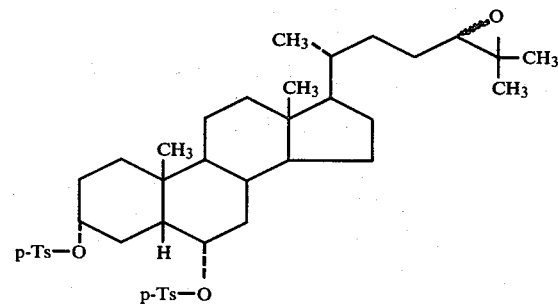

in dimethylformamide solution with an aqueous solution of potassium acetate, heating the resulting solution to about 100°–110° C. until the p-tosylate in the 3-position is replaced by an acetoxy group and a 5,6-double bond is introduced to prepare a compound having the structure:

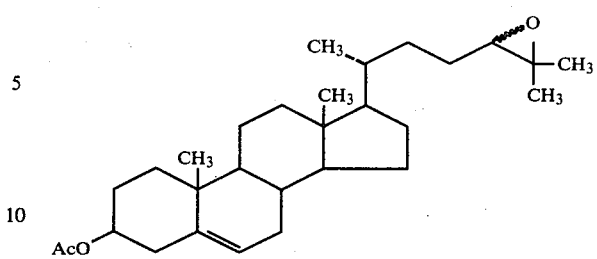

, dissolving said compound is tetrahydrofuran and mixing the resulting solution with 3 N-sulfuric acid at about 0° C. to prepare a mixture containing 3-acetyl-24R, 25-dihydroxycholesterol and 3-acetyl-24S, 25-dihydroxycholesterol.

12. In a process for preparing a steroid derivative, the steps of mixing a compound having the structure:

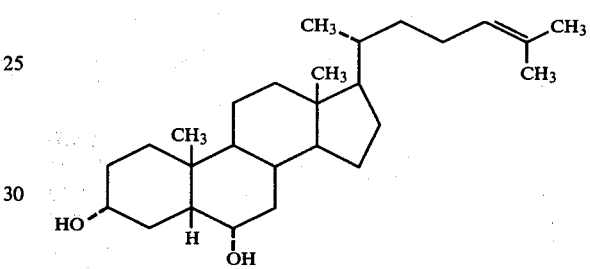

in pyridine solution with p-toluenesulfonyl chloride to prepare an ester compound having the structure:

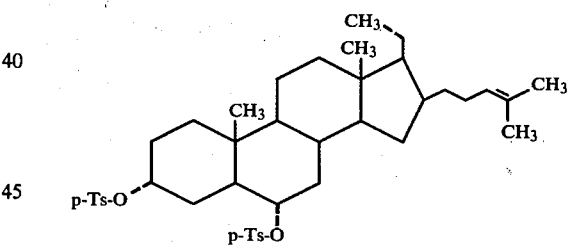

mixing said ester compound in methylene chloride solution with a solution of m-chloroperbenzoic acid to prepare an oxide compound having the structure:

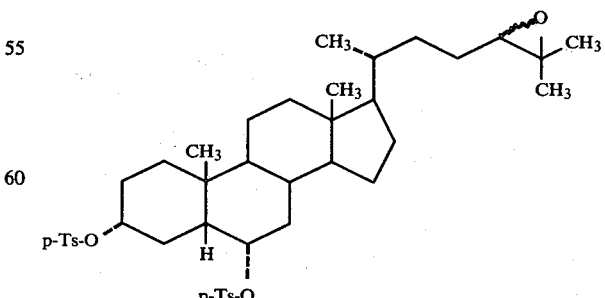

mixing said oxide compound in tetrahydrofuran solution with 3 N aqueous sulfuric acid at about 0° C. to prepare a 24-hydroxy compound having the structure:

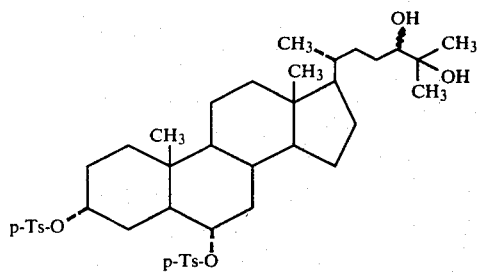
mixing said 24-hydroxy compound in dimethylformamide solution with an aqueous solution of potassium acetate, heating the resulting solution to from 100° to 110° C. until the p-tosylate in the 3-position is replaced by an acetoxy group and a 5,6-double bond is introduced, and by removing the 3-acetyl group to obtain 24R,25-dihydroxycholesterol and 24S,25-dihydroxycholesterol.
* * * * *